United States Patent
Renard et al.

[11] Patent Number: 6,015,491
[45] Date of Patent: Jan. 18, 2000

[54] APPARATUS FOR PRESSURE EQUALIZATION AND FLUSHING IN A VESSEL

[75] Inventors: Pierre Renard, Saint nom la Breteche; Olivier Callebert, Rueil Malmaison; Jean Paul Dessapt, Beynes, all of France

[73] Assignee: Institut Francais du Petrole, Rueil Malmaison, France

[21] Appl. No.: 08/972,894

[22] Filed: Nov. 18, 1997

[30] Foreign Application Priority Data

Nov. 19, 1996 [FR] France .................................. 96/14186

[51] Int. Cl.⁷ .................................................. B01D 15/08
[52] U.S. Cl. ...................... 210/198.2; 210/656; 210/659; 210/661; 210/662; 210/198.1; 210/287; 137/592
[58] Field of Search .................................... 210/656, 659, 210/198.1, 198.2, 661, 209, 287, 662; 137/592

[56] References Cited

U.S. PATENT DOCUMENTS

| | | |
|---|---|---|
| 2,985,589 | 5/1961 | Broughton et al. . |
| 3,946,104 | 3/1976 | Förster et al. ........................... 423/659 |
| 4,498,991 | 2/1985 | Oroskar . |
| 5,156,736 | 10/1992 | Schoenrock . |
| 5,176,832 | 1/1993 | Dorta et al. . |
| 5,284,992 | 2/1994 | Hotier et al. . |
| 5,415,773 | 5/1995 | Noe ........................................ 210/264 |
| 5,610,322 | 3/1997 | Unger et al. . |
| 5,683,575 | 11/1997 | Yates et al. . |
| 5,736,259 | 4/1998 | Oda et al. . |

FOREIGN PATENT DOCUMENTS

| | | |
|---|---|---|
| 0 679 421 | 11/1995 | European Pat. Off. . |
| 0 688 589 | 12/1995 | European Pat. Off. . |
| 0 688 590 | 12/1995 | European Pat. Off. . |

*Primary Examiner*—W. L. Walker
*Assistant Examiner*—Michael Fleming
*Attorney, Agent, or Firm*—Millen, White, Zelano & Branigan

[57] ABSTRACT

An apparatus for equalising pressure and flush in a vessel (1) has a chromatographic separation chamber (5), a distribution plate (3) or collection plate located in the vessel, a pressure equalisation chamber (4) defined at least in part by the extremity of the vessel and by a first face of the plate, the separation chamber (5) being defined by a second face of the distribution or collection plate, a first conduit (6) which places a first fluid in communication with the distribution or collection plate, the separation chamber (5) communicating with the equalisation chamber (4) via a flush chamber (10) comprising a first opening (21). A line (9) for supplying a second fluid which is substantially pure or substantially non contaminated is directly connected to the flush chamber at a point such that a portion of the second fluid can circulate towards the pressure equalisation chamber via a further opening (20) and the remaining portion can circulate towards the separation chamber via the first opening (21). The pressure equalisation chamber (4) is connected to a means (14) for evacuating the fluid it contains.

16 Claims, 1 Drawing Sheet

APPARATUS FOR PRESSURE EQUALIZATION AND FLUSHING IN A VESSEL

The invention concerns a reactor comprising at least one internal partition, generally of metal, delimiting two compartments in which two fluids, which may or may not be different, circulate and in which pressure variations may occur either side of the partition.

The invention also concerns a process for flush the heads of a reactor isolated by a partition and undergoing a minimal pressure variation which is generally in sudden jolts.

More particularly, it is applicable to a simulated moving bed apparatus, for example an apparatus for chromatographic adsorption of a mixture of xylenes to separate para-xylene or a mixture of aliphatic hydrocarbons to separate n-alkanes from isoalkanes or n-alkenes from isoalkenes.

This type of adsorption apparatus will be used as an example in the present application.

Above a certain diameter (for example above 1 m) in a pressurised reactor, the heads are generally elliptical or hemispherical in form to provide better mechanical tolerance of pressure.

In certain cases the reaction portion does not or cannot directly follow the shape of these heads.

This is the case, for example, with reactors using liquid or gas chromatography where the lower and upper surface of the adsorbent beds must be perfectly flat to obtain a fluid front which is as flat as possible.

Process requirements dictate that in this case, the reaction section must be isolated from the volume constituted by the head(s) by means of an internal partition of appropriate shape, a flat partition provided with a grid in the case of liquid or gas chromatography:

The flat partition isolates the process fluid from the fluid contained in the head(s).

a grid located near the partition and substantially parallel to the flat partition holds the adsorbent in the volume intended for it, while allowing circulation of fluid through the bed and its external collection, or its injection from outside the reactor.

The shape of this internal partition is not suitable for supporting pressure and thus the pressures either side of the partition, namely the process side and the head side, must be equalised.

The simplest method for equalising the pressures is to provide an opening through the partition: the slightest difference in pressure immediately results in a transfer of fluid and the system rapidly equalises particularly when the fluid is a liquid.

However, in certain processes such as simulated moving bed chromatography, the fluid which circulates on the process side during a cycle is sometimes pure and sometimes impure, and further, slight jolts in pressure, which are inherent to the process, occur due to the opening and closing of valves and to changes in flow rate, and thus matter is transferred through the opening in the partition during a cycle.

Thus the volume of fluid contained in a head gradually becomes contaminated, each jolt in pressure causing a transfer of pure or impure fluid through the opening provided in the partition, from the adsorption zone.

Conversely, the contaminated volume contained in the head can contaminate the process fluid when the latter is pure and at the moment in the cycle when there is a jolt in pressure.

In order to avoid this phenomenon, one solution is to inject a clean flush fluid into the head concerned.

This solution can be envisaged for a small diameter but is impractical for larger diameters: since the flush flow rate is very small compared with the volume of the head, if it is accidentally contaminated, the contamination is spread by mixing in the whole of the volume of the head and the flush fluid cannot rapidly replace the contaminated volume with clean flush fluid unless a very high flush flow rate is used, which is incompatible with the process, as this flow will add to the process fluid.

In order to improve the equalisation apparatus by causing a minimum of contamination, United States patent U.S. Pat. No. 5,415,773 describes the following arrangement:

The opening in the partition is prolonged by a confinement conduit with a minimum volume calculated so that the interface between the process fluid on the adsorbent side and the fluid on the head side remains in that volume during jolts in pressure. According to that patent, contamination is normally limited to that conduit.

Further, the confinement volume in the conduit is connected to a flush chamber, one end of which is completely open, going into the head, and the other end of which is connected to an external purge line.

An external flush fluid is continuously injected at a rate which is equal to or very slightly higher than the purge rate.

In this way:
the flow rate of the flush fluid sent to the process fluid through the opening in the partition is zero or reduced to a minimum;
any accidental contamination with a volume greater than that of the confinement conduit (the process fluid/flush fluid interface is accidentally displaced over the conduit) is entrained and flushed into the flush chamber then evacuated by the flush line to an external point.

This apparatus has the following disadvantages:

While the flush fluid injected is a clean fluid, the head volume (equalisation chamber) cannot be prevented from becoming partially contaminated by existing leaks of process fluid:
at the internal partition composed of several elements assembled and disposed side by side and never perfectly sealed;
at the conduit (or manifold) which circulates the process fluid through the head from outside to the adsorbent bed (or vice-versa). The conduit can be composed of elements assembled together by flanges which may be the source of leaks.

All of this contamination can be partly transferred via the confinement conduit, the opening and non-sealed portions of the partition, into the process fluid, thus deleteriously affecting purity.

Since the volume of the confinement conduit is very small, it cannot confine the contamination within that volume in all cases. The process fluid/flush fluid interface can in certain cases be displaced such that, in particular in the case of a large diameter reactor, it is sometimes clearly in the flush chamber, sometimes clearly in the adsorption zone, which automatically causes reciprocal contamination of the process side product and flush chamber side product.

Seeking a nil or minimum flow rate for the flush fluid through the opening in the partition means that the injected flush flow rate is very close to or equal to the purge flow rate, and that there is no significant difference in pressure (no controlled overpressure) between the head (equalisation chamber) and the process section. Since that pressure difference is not controlled, there is always a risk of contamination from the equalisation chamber to the process portion (or vice versa) through all existing openings: the opening in the partition, openings due to imperfect assembly of the parts constituting the partition, or the manifold.

The prior art is illustrated in U.S. Pat. No. 3,946,104.

One aim of the invention is to overcome the disadvantages mentioned above.

A further aim of the invention is to provide a pressurised reactor comprising flat distribution plates or partitions, which substantially eliminates the problems associated with top and/or bottom flushing in a reactor.

A further aim of the invention is to improve the performances of a simulated moving bed, in particular when using very large diameter reactors.

More precisely, the invention concerns an apparatus for equalising pressure and flush in a vessel having at least one concave extremity, the vessel comprising a chromatographic separation chamber or a reaction chamber, at least one distribution or collection plate located in the vessel, a pressure equalisation chamber defined at least in part by the extremity of the vessel and by a first face of the plate, the separation or reaction chamber being at least partially defined by a second face of said distribution or collection plate, a first conduit which places a first fluid in communication with the distribution or collection plate, the separation or reaction chamber communicating with the equalisation chamber via a flush chamber comprising a first opening, the apparatus being characterized in that a line for supplying a second fluid which is substantially pure or substantially non contaminated is directly connected to the flush chamber at a point such that a portion of said second fluid can circulate towards the pressure equalisation chamber via a further outlet opening and the remaining portion can circulate towards the separation or reaction chamber via the first opening, and in that said pressure equalisation chamber is connected to a means for evacuating the fluid it contains.

The second fluid, introduced laterally into the flush chamber, is generally a desorption fluid for the desired product, the desired product itself, for example para-xylene, or a mixture thereof, for example toluene and para-xylene.

The inventive combination of a flush chamber and a distribution plate has the following advantages: by directly introducing a non contaminated fluid into the flush chamber, for example solvent, fluid originating from the pressure equalisation chamber does not penetrate into the adsorption chamber, which fluid could be contaminated by products from any leakage in the partition, the distribution plate or the hydrocarbon distribution circuit entering the section of the chromatographic column adjacent the distribution plate. Any contamination would deleteriously affect purity.

The flush chamber can be substantially tubular.

The line supplying the second fluid can be connected to the flush chamber at a point corresponding to a volume inside the chamber or tube which represents 30% to 90% of the total volume of the flush chamber, this volume being determined from the face of the distribution plate. Better results are observed when the point connecting the supply line to the flush chamber corresponds to a volume representing 50% to 80% of the total volume of the chamber. Under these conditions, during jolts in pressure, the volume of the zone contaminated by principal fluid rising into the flush chamber will always be smaller than this keeper volume and thus will not contaminate the pressure equalisation chamber. In other words, a portion of the second fluid will circulate towards the adsorption chamber but when an overpressure occurs in the equalisation chamber at the distribution plate, principal fluid from the adsorption chamber is temporarily introduced into the keeper volume of the flush chamber without exceeding it, and when equilibrium is re-established it is returned with the second fluid to the adsorption chamber. On average, a portion of the second fluid will always circulate in the same direction (towards the adsorption chamber) and there will thus be no transfer of principal fluid from the adsorption chamber to the pressure equalisation chamber.

The flush chamber, and more particularly the contamination keeper or confinement volume is calculated as a function of the maximum fluctuations in pressure, i.e., the deformation of the partition of the distribution or collection plate following pressure fluctuations.

This volume is at most equal to:

$V (cm^3) = S (m^2) \times 0.01 (m)$, S being the cross section of the reactor; preferably at most $S \times 0.001$, which covers the largest transfers of fluids through the partition opening induced by jolts in the process pressure, in the case of very large diameter reactors.

The flush flow rate is generally substantially and significantly higher than the purge flow rate to ensure a permanent positive flow of clean fluid towards the process side through the partition opening.

The following is thus produced:

Systematic flush of the keeper or confinement volume by clean fluid.

A slight controlled overpressure in the pressure equalisation chamber with respect to the process side. Thus if there are leaks in the assembled portions of the partition or manifold, they are always composed of clean fluid which cannot contaminate the process.

In this way, any leaks of fluid from the flush chamber to the process side through imperfections in the assembly of the partition are preferably composed of clean fluid.

In one advantageous feature of the apparatus, the flush chamber, preferably a tubular chamber, comprises an outlet opening on the pressure equalisation chamber side which is in the immediate vicinity of the face of the plate, which means that a clean fluid can better flush unwanted products originating from any leaks close to the distribution or collecting plate and which are concentrated at this level and keep the fluid near the partition clean. This drainage is all the more effective when the means for evacuating fluid contained in the pressure equalisation chamber is also located in the immediate proximity of the plate and preferably in a direction which is substantially diametrically opposite to that taken by the fluid leaving the outlet opening from the flush chamber.

The preferred U shape, for example, further improves drainage into the lower portion of the pressure equalisation chamber.

This flushing and pressure equalisation apparatus is of particular use in chromatographic separation processes, for example by adsorption on an adsorbent, in catalytic processes and in reactive adsorption processes, using a particulate solid. It can be carried out in the presence of a gaseous, liquid, mixed, supercritical or subcritical fluid.

It can also be applied to processes which do not involve the use of particulate solids.

It is of particular application in the liquid phase, in particular in a simulated moving bed adsorption process such as those described in U.S. Pat. No. 2,985,589, U.S. Pat. No. 4,498,991, European patents EP-A-0,679,421, EP-A-0, 688,590, EP-A-0,688,589 and U.S. Pat. No. 5,284,992 which are hereby incorporated by reference, during which sharp pressure variations occur due to the successive opening and closing of valves.

The invention also concerns a process for equalising pressure and flush in an apparatus for chromatographic separation, for example by adsorption, of a mixture of compounds on a particulate solid (adsorbent) to separate at least one of the compounds. More precisely, the process concerns the top and/or bottom of a reactor which is separate from the chromatographic separation zone or the reaction zone by a distribution or collection plate, depending on the case.

In more detail, the invention concerns a process for equalising pressure and flushing in a chromatographic separation chamber or in a reaction chamber comprising, at one extremity, a pressure equalisation zone, and a chromatographic or reaction chamber in which a first fluid (process fluid) is circulated via a distribution or collection plate separating the pressure equalisation zone from the chromatographic or reaction zone, the process being characterized in that a second fluid selected from the group formed by a solvent, a desired product and a mixture thereof, is circulated in a flush zone which places the chromatographic or reaction zone in communication with the pressure equalisation zone, by introducing the second fluid into the flush zone via a direct lateral connection, such that a portion of the second fluid circulates from said flush chamber towards the pressure equalisation chamber and the remaining portion of the second fluid circulates from the flush chamber towards the chromatographic or reaction chamber, and in that a quantity of fluid originating from the pressure equalisation chamber is evacuated, which quantity corresponds to the quantity of fluid leaving the flush zone.

The particulate solid can be an adsorbent in the case of a chromatographic zone or a catalyst in the case of a reaction zone. In some cases, the reaction zone may not contain particulate solids.

The second fluid can be introduced into the flush chamber at a rate $d_1$, of at most 0.2% of the rate corresponding to the first fluid distributed in the first section of the column in contact with the distribution plate. This rate $d_1$, is advantageously at most 0.1% of the rate of the first fluid, in particular in the range 0.02% to 0.05%.

The rate $d_1$, of the second fluid penetrating directly into the flush chamber can be fixed and the rate $d_2$ of the fluid leaving the pressure equalisation chamber is controlled such that the rate $d_3$ of the second fluid flowing into the adsorption chamber via the flush chamber outlet opening is at least 5% of the rate $d_3$, of the second fluid introduced into the flush chamber. This rate $d_3$ is advantageously at least 10%, and preferably in the range 40% to 60%, of rate $d_1$.

The invention will be better understood from the accompanying drawings which schematically illustrate an embodiment of the apparatus and an implementation of the process. In the drawings.

Figure 1:
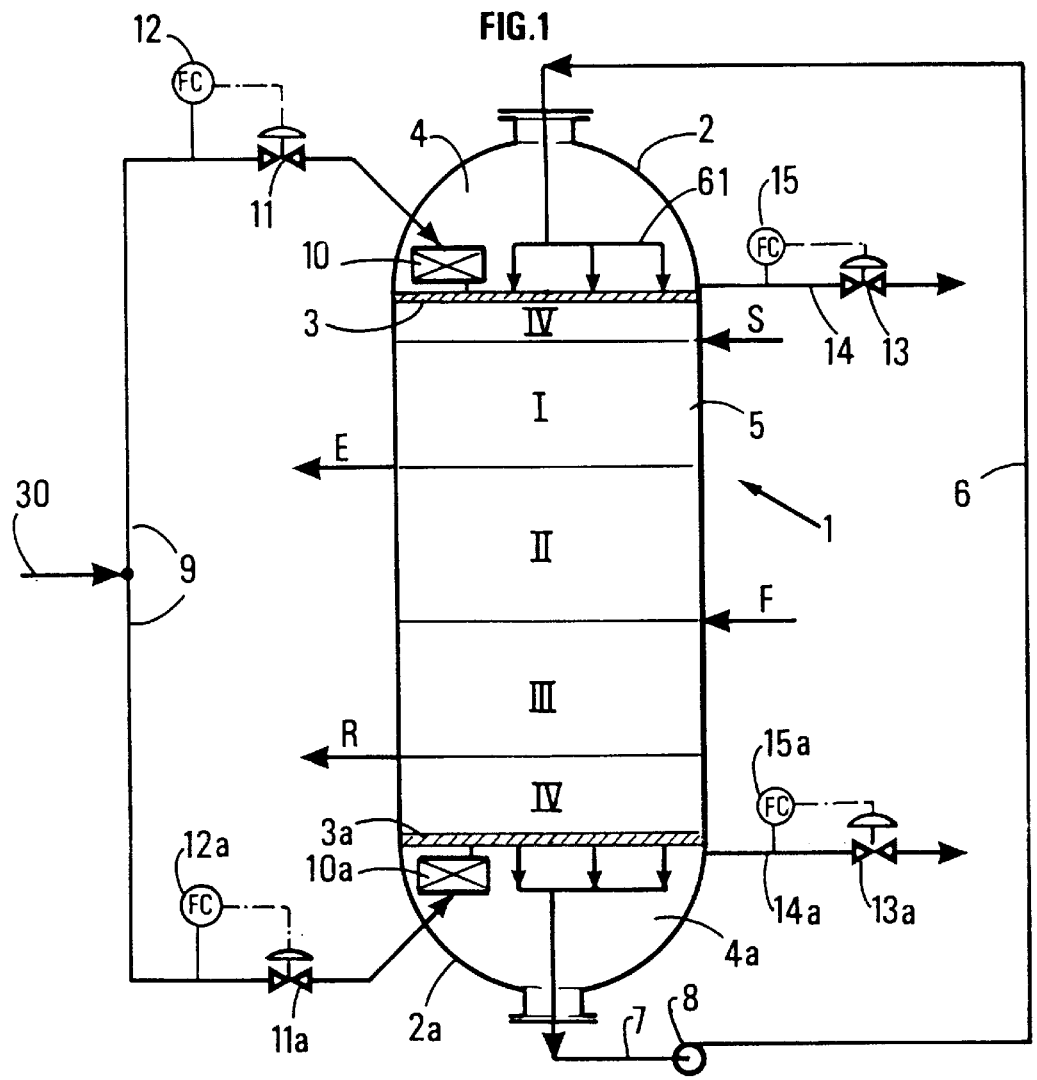
FIG. 1 shows an axial cross section of a simulated moving bed adsorption chamber in which the top and bottom respectively contain a pressure equalisation chamber combined with a flush chamber communicating with the adsorption chamber.
Figure 2:
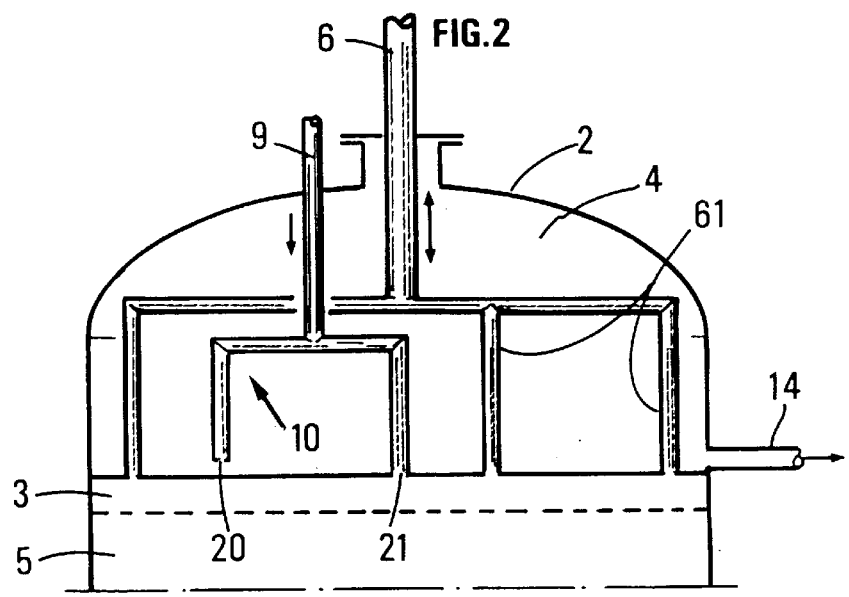
FIG. 2 shows in more detail a longitudinal section of the top of a separation chamber comprising the apparatus of the invention.

In FIG. 1, an elongate cylindrical shell 1 has a hemispherical head 2 at one extremity, comprising a distribution plate 3 for a principal fluid supplied via a line 6 and a plurality of distribution lines 61 (see FIG. 2). The distribution plate separates a pressure equalisation chamber 4 from an adsorption chamber 5 below the plate and supplies the adsorption chamber. Adsorption chamber 5 operates as a simulated counter-current moving bed and comprises a plurality of column sections, for example 24, filled with a zeolitic adsorbent such as an X or Y zeolite exchanged with barium and defining four zones:

a desorption zone I between a solvent supply point 5 and an extract withdrawal point E;

a purification zone II between a feed supply point F and an extract withdrawal point E;

an adsorption zone III between a raffinate withdrawal point and the feed supply point F;

a buffer zone IV between the solvent supply point S and the raffinate withdrawal point R.

In FIG. 1, the fluid leaving one column section of zone IV via a collection plate, collection lines (not shown) and a recycle line 7 are sent via a pump 8 and line 6 to the top of the adsorption chamber for re-distribution to the distribution plate 3 to a further column section of zone IV.

In the hemispherical head containing the pressure equalisation chamber 4, a U-shaped flush chamber 10 is supplied via a direct line 9 with a desorbent such as toluene from a supply 30. An evacuation line 14 continuously extracts the fluid contained in the pressure equalisation chamber. Flow control means 12 and 15 comprising regulating valves 11 and 13 in lines 9 and 14 respectively control the flow rate of the desorbent introduced directly into the flush chamber and that of the fluid extracted directly from the pressure equalisation chamber.

In more detail, in FIG. 2, the upper head 2 with a hemispherical or elliptical shape closes the upper extremity of chamber 1. The first face of distribution plate 3 defines the pressure equalisation chamber 4 extremity while the second face of the plate defines the upper limit of the adsorption chamber itself 5 which contains adsorbent. Line 6 supplies distribution plate 3, via a manifold 61, with a principal fluid (process fluid) which is that derived from the last contact zone with the lower distribution plate, in this case zone IV. The former distribution plate supplies the adsorbent in chamber 5 with this principal fluid.

The flush chamber 10 contained in the pressure equalisation zone 4 directly receives desorbent at a rate $d_1$, from line 9, by a direct connection, preferably perpendicular, which is carefully located between a first outlet opening 21 from the flush chamber in contact with the distribution plate and a second outlet opening 20. This outlet opening 20 is advantageously located in the immediate vicinity of the distribution plate and close to its periphery. A portion of the desorbent originating from line 9 penetrates into the pressure equalisation chamber via opening 20 at a rate $d_2$. It partially mixes with fluid from the pressure equalisation chamber which normally contains desorbent and possibly impurities due to the multitude of small leaks from the distribution plate and the distribution circuit 61 for the principal fluid the composition of which changes periodically with the cycle of supply and extraction to and from the column sections.

The remaining portion of the desorbent from line 9 flows from the flush chamber towards distribution plate 3 and towards the adsorbent of reactor 5 at flow rate $d_3$, through outlet opening 21 in contact with the plate. It typically represents on average 50% of the flow rate of the desorbent from line 9.

The flow rate $d_2$ of desorbent passing through outlet opening 20 is evacuated with the contaminating impurities via outlet channel 14 located at the external wall of equalisation chamber 4. This extraction of fluid at flow rate $d_2$ is all the more effective when the channel is positioned near the distribution plate, preferably at a point which is substantially diametrically opposite the fluid inlet at flow rate $d_2$ penetrating into chamber 4. The fluid stream carries out a washing action which drains the contamination essentially concentrated in the vicinity of the distribution plate.

The pressure equalisation and flush apparatus operates as follows. A desorbent flow rate $d_1$, is generally fixed at most at 0.1% of the flow rate of the principal fluid entering adsorption chamber 5, by means of control valve 11 and flow rate regulator 12. A flow rate $d_2$ for fluid outlet from the pressure equalisation chamber is regulated by a regulating valve 13 and regulator 15, under conditions such that on average a flow $d_3$ of desorbent with a composition which is identical to that of the desorbent supplied via line 9 flows from the flush chamber to the adsorbent via opening 21.

This disposition and mode of operation can also control the pressures either side of the distribution plate. When an underpressure occurs in the adsorption chamber, the membrane (or partition) of distributor plate 3 deforms, which causes the process fluid to rise temporarily in the flush chamber, at most to the junction of line 9 with this chamber. The volume occupied by the process fluid represents 50% to 80% of the total volume of the flush chamber. The practically instantaneous return to equilibrium results in a return of the process fluid in the keeper volume into the adsorption chamber so that no trace of process fluid is evacuated into equalisation chamber 4 via outlet opening 20.

The upper head of the reactor has been described, but as FIG. 1 shows, the same means can be present at the lower head of the reactor, shown with the same reference numerals (with an added a, for example 2a, 3a, 4a). The distribution plate becomes a principal fluid collection plate associated with a collection manifold and the principal fluid leaving the last zone is recycled to the top head of the reactor by means of a recycle line 7 and pump 8. A flow $d_1$ of desorbent or other pure product which may be the same as or different to that introduced to the top is introduced directly and laterally into flush chamber 10a. This flow $d_1$ is divided into a flow $d_2$ circulating into equalisation chamber 4a via flush chamber 10a and a flow $d_3$ passing through the outlet opening in collection plate 3a, in communication with adsorption chamber 5. The fluid contained in the pressure equalisation chamber is extracted at a rate $d_2$ via an evacuation line 14a.

The preceding examples can be repeated with similar success by substituting the generically or specifically described reactants and/or operating conditions of this invention for those used in the preceding examples.

The entire disclosure of all applications, patents and publications, cited above and below, and of corresponding French application No. 96/14.186, are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

We claim:

1. An apparatus for equalising pressure and flush in a vessel (1) having at least one concave extremity, the vessel comprising a chromatographic separation chamber (5) or a reaction chamber, at least one distribution plate (3) or collection plate located in the vessel, a pressure equalisation chamber (4) defined at least in part by the extremity of said vessel and by a first face of the plate, the separation chamber (5) or reaction chamber being at least partially defined by a second face of said distribution or collection plate, a first conduit (6) which places a first fluid in communication with the distribution or collection plate, the separation or reaction chamber (5) communicating with the equalisation chamber (4) via a flush chamber (10) comprising a first opening (21), the apparatus being characterized in that a line (9) for supplying a second fluid which is substantially pure or substantially non contaminated is directly connected to the flush chamber at a point such that a portion of said second fluid can circulate towards the pressure equalisation chamber via a further outlet opening (20) and the remaining portion can circulate towards the separation or reaction chamber via the first opening (21), and in that said pressure equalisation chamber (4) is connected to a means (14) for evacuating the fluid it contains.

2. An apparatus according to claim 1, in which the flush chamber is tubular.

3. An apparatus according to claim 1, in which the line (9) supplying the second fluid is connected to the flush chamber (10) at a point corresponding to a volume inside the flush chamber which represents 30% to 90% of the total volume of the flush chamber, this volume being determined from the first face of the plate, so that there is no transfer of first fluid from the separation or reaction chamber (5) to the pressure equalisation chamber via the opening (21).

4. An apparatus according to claim 3, in which said connection point corresponds to a volume representing 50% to 80% of the total volume of the flush chamber.

5. An apparatus according to claim 1, in which the flush chamber comprises an outlet opening (20) on the pressure equalisation side, in the immediate vicinity of the first face of the plate.

6. An apparatus according to claim 2, in which the means (14) for evacuating fluid from the pressure equalisation chamber is located in the immediate vicinity of said first face of the plate.

7. An apparatus according to claim 5, in which the outlet opening (20) from the flush chamber, on the pressure equalisation side, is substantially diametrically opposite the means (14) for evacuating fluid from the pressure equalisation chamber.

8. An apparatus according to claim 1, in which the chromatographic separation chamber is a simulated moving bed.

9. A process for equalising pressure and flushing in a chromatographic separation chamber or in a reaction chamber comprising, at one extremity, a pressure equalisation zone (4), and a chromatographic or reaction zone (5) in which a first fluid (6) (process fluid) is circulated via a distribution plate (3) or collection plate (3a) separating the pressure equalisation zone from the chromatographic or reaction zone, the process being characterized in that a second fluid (9) selected from the group formed by a solvent, a desired product and a mixture thereof, is circulated in a flush zone (10) which places said chromatographic or reaction zone in communication with the pressure equalisation zone, by introducing said second fluid into the flush zone via a direct connection, such that a portion of the second fluid circulates in said flush chamber (4) towards the pressure equalisation chamber and the remaining portion of the second fluid circulates from the flush chamber towards the chromatographic or reaction zone (5), and in that a quantity of fluid originating from the pressure equalisation chamber is evacuated, which quantity corresponds to the quantity of fluid leaving the flush zone.

10. A process according to claim 9 in which the direct connection to the flush zone is positioned so as to determine a keeper volume between the connecting point and the distribution or collection plate, representing 30% to 90% of the volume of the flush zone and sufficiently large for there to be no fluid transfer from the chromatographic or reaction zone to the pressure equalisation zone during sudden variations in pressure.

11. A process according to claim 9, in which the second fluid is introduced at a flow rate $d_1$, of at most 0.2% of the corresponding flow rate of the first fluid.

12. A process according to claim 9 in which a flow rate $d_1$, of the second fluid (9) penetrating directly into the flush zone is fixed, and a flow rate $d_2$ of fluid (14) leaving the pressure equalisation zone is controlled so that a flow rate $d_3$ of the second fluid via the opening (21) flowing into the chromatographic or reaction zone (5) is at least 5% of flow rate $d_1$.

13. A process according to claim 9 for chromatographic separation of a mixture of hydrocarbons comprising xylenes.

14. A process to claim 9 for the chromatographic separation of a mixture of aliphatic hydrocarbons.

15. A process according to claim 9 in which a flow rate $d_1$ of the second fluid (9) penetrating directly into the flush zone is fixed, and a flow rate $d_2$ of fluid (14) leaving the pressure equalisation zone is controlled so that a flow rate $d_3$ of the second fluid via the opening (21) flowing into the chromatographic or reaction zone (5) is at least 10% of the flow rate $d_1$.

16. A process according to claim 9 in which a flow rate $d_1$, of the second fluid (9) penetrating directly into the flush zone is fixed, and a flow rate $d_2$ of fluid (14) leaving the pressure equalisation zone is controlled so that a flow rate $d_3$ of the second fluid via the opening (21) flowing into the chromatographic or reaction zone (5) is in the range of about 40% to about 60% of flow rate $d_1$.

* * * * *